US012788527B2

(12) United States Patent
Gorka

(10) Patent No.: US 12,788,527 B2
(45) Date of Patent: Nov. 10, 2026

(54) OPHTHALMIC SURGERY DEVICE FOR EYE GUIDANCE AND ASSOCIATED METHODS

(71) Applicant: OcuGuide LLC, Salt Lake City, UT (US)

(72) Inventor: Joanna Eve Gorka, Tucson, AZ (US)

( * ) Notice: Subject to any disclaimer, the term of this patent is extended or adjusted under 35 U.S.C. 154(b) by 147 days.

(21) Appl. No.: 18/638,022

(22) Filed: Apr. 17, 2024

(65) Prior Publication Data

US 2024/0350223 A1 Oct. 24, 2024

Related U.S. Application Data

(60) Provisional application No. 63/496,695, filed on Apr. 18, 2023.

(51) Int. Cl.
*A61B 3/00* (2006.01)
*A61B 90/20* (2016.01)
*G16H 40/67* (2018.01)

(52) U.S. Cl.
CPC ............ *A61B 90/20* (2016.02); *A61B 3/0091* (2013.01); *G16H 40/67* (2018.01)

(58) Field of Classification Search
CPC ........................... G02B 21/00; G02B 21/0004; G02B 21/0032; G02B 21/06; G02B 21/24; G02B 21/36; G02B 21/361; G16H 40/67; A61B 90/20; A61B 3/0091; A61B 3/0008; A61B 90/30; A61B 2090/309; A61B 90/35; A61B 90/36
USPC ............... 359/385, 362, 368, 387, 388, 390; 351/205, 221; 600/249
See application file for complete search history.

(56) References Cited

U.S. PATENT DOCUMENTS

| | | | |
|---|---|---|---|
| 4,478,499 A | 10/1984 | Hoerenz | |
| 5,293,532 A | 3/1994 | Marshall | |
| 5,312,393 A | 5/1994 | Mastel | |
| 5,331,149 A | 7/1994 | Spitzer et al. | |
| 5,947,955 A | 9/1999 | Kadambi et al. | |
| 6,312,128 B1 | 11/2001 | Doisy, III | |
| 7,513,621 B2 | 4/2009 | Nevyas et al. | |
| 2013/0038835 A1* | 2/2013 | Kitajima | A61B 3/14 351/206 |
| 2013/0250236 A1 | 9/2013 | Tsai et al. | |

FOREIGN PATENT DOCUMENTS

CN 113703146 A * 11/2021 ......... G02B 21/0004

* cited by examiner

*Primary Examiner* — Arnel C Lavarias
(74) *Attorney, Agent, or Firm* — John P. Davis; Thayne and Davis LLC

(57) ABSTRACT

Embodiments of the disclosed systems and methods provide for an eye fixation assistance device, an associated control system, and method of using the same. In various embodiments, the eye fixation assistance device may comprise a base plate which may be attached to a microscope used for ophthalmic surgery via a suitable attachment mechanism. A fixation point array may be attached and/or otherwise coupled to the base plate that comprises a plurality of selectively illuminable light sources, with each light source defining a potential eye fixation point for a patient. A control system may be used to selectively illuminate one or more of the plurality of light sources. A patient may perceive which light source(s) is/are illuminated, corresponding a desired fixation point for the patient's eye during at least part of procedure, and orient and/or otherwise direct their eyes to the illuminated fixation point(s).

18 Claims, 15 Drawing Sheets

OPHTHALMIC SURGERY DEVICE FOR EYE GUIDANCE AND ASSOCIATED METHODS

CROSS-REFERENCE TO RELATED APPLICATIONS

This application claims the benefit of priority under 35 U.S.C. § 119(e) to U.S. Provisional Application No. 63/496,695, filed Apr. 18, 2023, and entitled "OPHTHALMIC SURGERY DEVICE FOR EYE GUIDANCE," which is hereby incorporated by reference in its entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

SUMMARY OF THE INVENTION

The present disclosure relates generally to ophthalmic surgical devices and associated methods. More specifically, but not exclusively, the present disclosure relates to ophthalmic surgical devices and associated methods that assist a surgical professional in directing patient eye positioning.

Ophthalmic surgeries and/or procedures are relatively common in eye care. Such procedures include, for example and without limitation, cataract removal, intraocular lens insertion, glaucoma-treating trabeculectomy, glaucoma-treating drainage stent insertion, refractive intraocular surgery, and canaloplasty. Many individuals are vulnerable to developing cataracts that require surgery as they age. Indeed, more than 4 million cataract surgeries are performed annually in the United States and over 20 million worldwide. Glaucoma and refractory error are also relatively common ophthalmic conditions necessitating surgery to correct.

Generally, an eye to be operated on is anesthetized with topical eye drops to ensure a relatively painless procedure. An eyelid speculum may be used to keep the eye open. In many procedures, the patient receives an oral dose or intravenous infusion of benzodiazepine to promote a relatively calm disposition and reduce anxiety during the procedure. Retrobulbar blocks may, in relatively rare cases, be used to achieve analgesia and akinesia. For the majority of intraocular and corneal surgeries, however, anesthetization is achieved using one or more of anesthetic topical drops and/or oral and/or intravenous benzodiazepine.

Many ophthalmic surgeries are performed on patients while they are awake with a patient's extraocular movement ability intact. Such surgeries often require patients to (i) follow directions by the surgeon to move their eye(s) to certain positions and/or orient them in a particular direction/position and (ii) hold the position for an extended period. Whether a patient closely follows such instructions impacts surgical success.

Following such directions, however, may present certain challenges to patients. For example, patients can struggle to obey verbal commands under the stress of surgery. Language and communication barriers may also contribute to the difficulty of a surgeon giving verbal commands that are followed by a patient. Verbal instructions may further be vague, ineffective, and/or otherwise imprecise when attempting to achieve precise eye position. Moreover, even if desired positional movements of the eye are initially achieved, patients may have trouble keeping their eye fixed in an arbitrary position as directed.

Many ophthalmic surgeries require delicate and precise maneuvers as the surgeon views the eye through a microscope and manually deploys instruments to the surface and/or inside of the eye. Unplanned and/or accidental movement of the instruments can cause trauma to the eye resulting in complications including but not limited to posterior capsule rupture, vitreous loss, cystoid macular edema, endophthalmitis, vitreous/suprachoroidal hemorrhage, retinal tears/detachment, and/or lens dislocation. In addition to damaging the eye, these complications may also prolong surgery and/or overall recovery times.

Conventional methods to direct and stabilize ocular fixation during surgery may be relatively invasive, uncomfortable, and/or may carry certain risks. For example, hooks and forceps may be used to grab a conjunctiva of the eye. These hooks and forceps may, however, cause tissue damage, increase the risk of bleeding, and/or may require manual stabilization. Similarly, fixation rings may require manual stabilization onto the eye and may be limited outside of holding the eye in a central orientation (i.e., looking straight) during a capsulorhexis step in cataract surgery.

In rare cases, nerve blocks such as peribulbar, sub tendon, and/or retrobulbar blocks may be used to paralyze the eye nerves during procedures. Nerve blocks, however, are invasive and can cause hemorrhage, globe perforation, nerve damage, and/or systemic effects including cardiovascular depression and/or brainstem anesthesia. Nerve blocks may also require the patient to hold very still during administration. General anesthetization may be performed in certain situations but has notable respiratory and cardiac risks.

Embodiments of the disclosed systems, methods, and/or associated devices may provide for relatively non-invasive, non-verbal solutions to assist ophthalmic surgery patients to fixate one or more eyes in a desired orientation during a procedure. In various embodiments, the disclosed systems, methods, and/or associated devices may present relatively lower risk compared with certain conventional techniques, be hands-free for the surgeon and/or other care providers, and/or be relatively versatile.

Consistent with various embodiments disclosed herein, an eye fixation assistance device, an associated control system, and method of using the same are described. In various embodiments, the eye fixation assistance device may comprise a base plate which may be affixed to a microscope used for ophthalmic surgery via a suitable attachment mechanism. The base plate may, in some embodiments, surround at least a portion of an optical objective and/or lens of the microscope and/or otherwise define an aperture and/or other opening through which the optical lens of the microscope may pass through and/or may not be optically blocked by the base plate.

A fixation point array may be attached and/or otherwise coupled to the base plate. In various embodiments, the fixation point array may comprise a plurality of light sources attached and/or coupled to the base plate in any suitable matter, with each light source defining a potential eye fixation point for a patient. In some embodiments, the fixation point array may be integral to the base plate. As detailed herein, the plurality of light sources of the fixation point array may be arranged in a variety of suitable patterns. Moreover, a variety of suitable types of light sources may be used including, for example and without limitation, light emitting diodes ("LEDs").

A control system, which in some embodiments may comprise a touch screen and/or other suitable control device and/or a mobile device running a suitable application, may be in communication with the plurality of light sources and be configured to selectively illuminate one or more of the plurality of light sources of the eye fixation assistance device. A patient may perceive which light source(s) is/are illuminated, corresponding a desired fixation point for the patient's eye during at least part of procedure, and orient and/or otherwise direct their eye(s) to the illuminated fixation point. In this manner, a patient may be directed to fix their eye in an orientation desired by a surgeon during an ophthalmic procedure.

BRIEF DESCRIPTION OF DRAWINGS

The inventive body of work will be readily understood by referring to the following detailed description in conjunction with the accompanying drawings, in which.

DETAILED DESCRIPTION OF THE INVENTION

Figure 1:
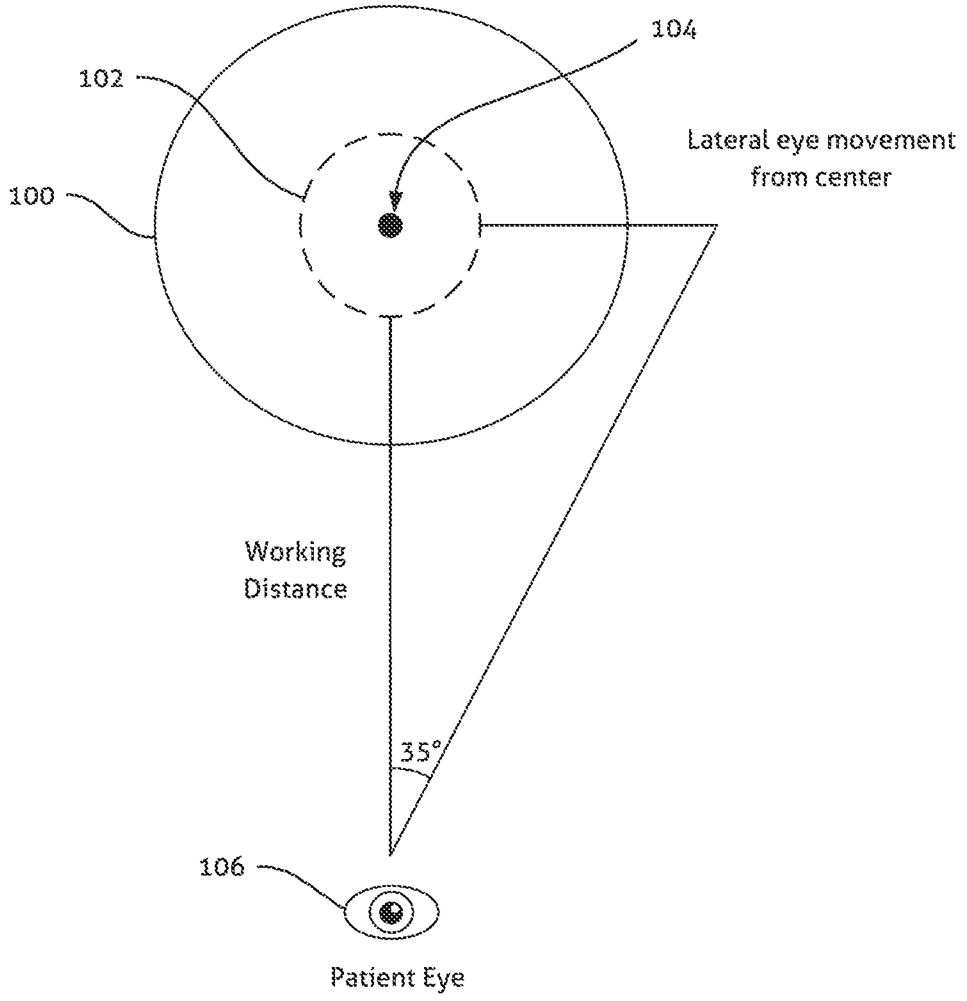
FIG. 1 illustrates a non-limiting example of a simplified diagram showing an orientation of an eye fixation assistance device relative to the center of a microscope lens consistent with certain embodiments of the present disclosure.

A description of systems and methods consistent with embodiments of the present disclosure is provided herein. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all these details. Moreover, for the purpose of clarity, certain technical material that is known in the related art has not been described in detail in order to avoid unnecessarily obscuring the disclosure.

The embodiments of the disclosure may be understood by reference to certain drawings where, in certain instances (but not necessarily all), like parts may be referred to by like numerical references. The components of the disclosed embodiments, as generally described and/or illustrated in the figures herein, could be arranged and designed in a wide variety of different configurations. Thus, the following description of the embodiments of the systems and methods of the disclosure is not intended to limit the scope of the disclosure but is merely representative of possible embodiments of the disclosure. In addition, the steps of any method and/or process disclosed herein do not necessarily need to be executed in any specific order, or even sequentially, nor need the steps be executed only once, unless otherwise specified. Moreover, it will be understood that, as used herein, a process and/or method that is described as being based on some information is not necessarily exclusively based on the information, but indeed may be based at least in part on the information and/or a portion thereof.

Consistent with various embodiments disclosed herein, an eye fixation assistance device is described comprising a base plate and a fixation point array. The base plate may be configured to attach and/or otherwise be secured to a microscope used for ophthalmic surgery and define an opening, which in some implementations may be a circular aperture, allowing the optical objective and/or lens of the microscope (which may generally be referred to herein for purposes of simplicity as a microscope lens and/or derivatives thereof) to view a patient's eye(s) without being obstructed by the base plate and/or other components of the eye fixation assistance device.

A fixation point array may be attached and/or otherwise coupled to the base plate that comprises a plurality of light sources (e.g., LEDs), with each light source defining a potential eye fixation point for a patient. In some embodiments, multiple LEDs functioning as a composite light source may be used for each light source. A control system, which may directly control the fixation point array and/or a microcontroller controlling the fixation point array, may be used to selectively illuminate one or more of the plurality of light sources of the eye fixation assistance device, directing a patient to orient their eye towards an illuminated fixation point.

FIG. 1 illustrates a non-limiting example of a simplified diagram showing an orientation of an eye fixation assistance device 100 relative to the center of a microscope lens 104 consistent with certain embodiments of the present disclosure. As illustrated, the center of a microscope lens 104 may be positioned an a suitable working distance from a patient's eye 106 for a procedure—that is, a suitable distance between the microscope lens and the patient's eye This working distance and a patient's ability to position the orientation of their eye 106 (i.e., the direction of their gaze) relative to this lens center 104 may provide a relative lateral degree of potential eye movement from the lens center 104, shown in the figure as a non-limiting example of 35°.

An eye fixation assistance device 100 may be positioned proximate to the center of the microscope lens 104. In certain embodiments, the eye fixation assistance device 100 may define an aperture 102 (i.e., an opening) that allows for the microscope to view the patient's eye 106 during a procedure without being obstructed by the eye fixation assistance device 100. It will be appreciated that the eye fixation assistance device 100 and/or the associated aperture 102 may be configured in a variety of ways that may depend, at least in part, on the configuration and/or geometry of the microscope. For example, the geometry of the aperture 102 may depend on the geometry of the lens 104 of the microscope. Although illustrated as a circular opening, the aperture 102 may in other embodiments define a variety of different shaped openings. For example, in further embodiments, the eye fixation assistance device 100 and, by extension, the aperture 102 may not completely surround and/or otherwise encircle the microscope lens, but may indeed only partially surround the microscope lens (e.g., as may be the case in a "U" shaped eye fixation assistance device 100).

In at least one non-limiting example, a radius of the eye fixation assistance device 100 of a 9 cm radius at a working distance of 20 cm may be sufficient to achieve a maximal lateral, off-center eye movement for average patients of an angle of 24°. The radius of the eye fixation assistance device 100 (and/or an associated base plate, as detailed below) of 9 cm may provide a full range of lateral eye movements for many procedures while remaining small enough to not obstruct the surgeon's workspace or otherwise be cumbersome. Larger eye fixation assistance devices 100 and/or associated base plates (e.g., devices having a larger radius) may be used for microscopes and/or procedures having a larger working distance, as the radius (or more generally, the geometric configuration) of the eye fixation assistance device 100 and/or associated base plates may be related to the working distance of the microscope.

Figure 2:
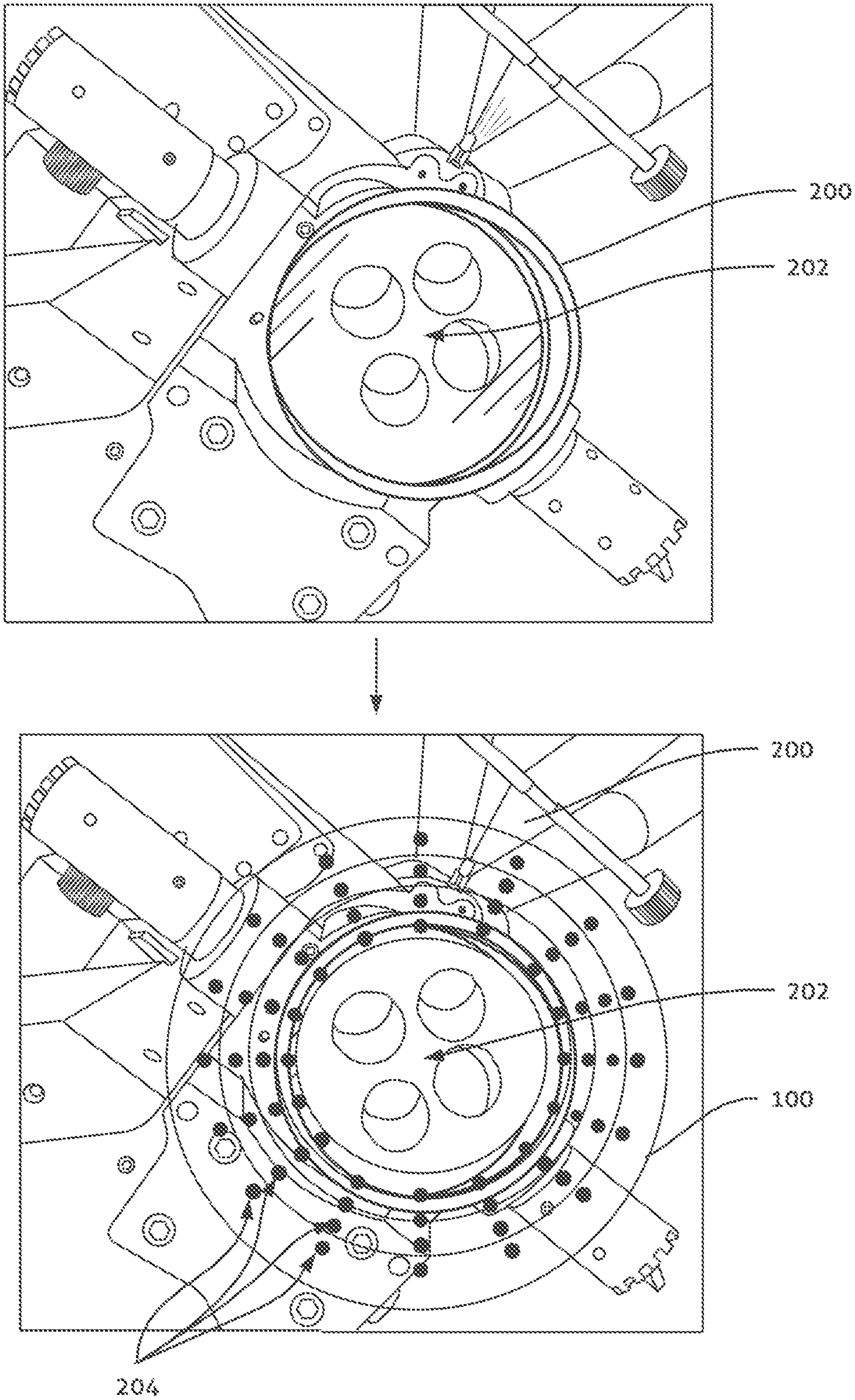
FIG. 2 illustrates a non-limiting example of an eye fixation assistance device illustrated from the perspective of a patient looking upwards towards a microscope lens consistent with certain embodiments of the present disclosure.

FIG. 2 illustrates a non-limiting example of an eye fixation assistance device 100 illustrated from a perspective of a patient looking upwards towards a microscope lens 202 consistent with certain embodiments of the present disclosure. As shown, a microscope 200 may comprise a microscope lens 202 which is oriented down towards a patient's eye during a procedure. Consistent with various disclosed embodiments, an eye fixation assistance device 100 (or more specifically, a base plate associated with the same) may be coupled, connected, and/or otherwise affixed via a suitable mechanism to the microscope 200. In various embodiments, the eye fixation assistance device 100 may be coupled to the microscope 200 in a manner such that the lens of the microscope 202 is not obstructed by the eye fixation assistance device 100 and/or portions thereof.

The eye fixation assistance device 100 may comprise a fixation point array comprising a plurality of light sources 204 at desired potential eye fixation points surrounding the microscope lens 202. The fixation point array and/or plurality of light sources 204 may be arranged in a variety of suitable patterns relative to the microscope lens 202. For example and without limitation, the fixation point array and/or plurality of light sources 204 may be arranged in a circle surround the microscope lens 202, in a plurality of concentric circles surrounding then microscope lens 202 and/or radial lines extending outwards from at least a portion of the microscope lens 202, in a cartesian grid, and/or in any other pattern defining a plurality of potential fixation points that may be used to help direct a patient to position their eye in a particular direction and/or orientation.

A variety of types of selectively illuminated light sources may be used in connection with the plurality of light sources 202. For example, in some embodiments, LEDs may be used. In certain embodiments, each fixation point of the fixation point array may be associated with a single LED, which may comprise a single color and/or color tunable LED source. In further embodiments, a plurality of individual LEDs may define each fixation point of the fixation point array. For example, in some embodiments, a fixation point may be associated with a plurality of LEDs (e.g., a cluster of LEDs), which indeed may be of a plurality different colors, allowing the fixation point to be selectively illuminated with one or more colors as desired by a surgical professional. Non-LED light sources may also be used including, for example and without limitation, traditional incandescent light sources.

In further embodiments, an electronic display and/or screen may be used in addition to and/or instead of an array of individual discrete light sources 202. For example, in some embodiments, the plurality of light sources 202 may be implemented by an electronic display and/or screen that allows for selection illumination of any portion of the display and/or screen. Embodiments using an electronic display and/or screen in connection with a fixation point array may provide a user with the ability to dynamically identify and/or illuminate fixation points across the screen instead of relying on fixed location fixation points, as may be the case in implementations where the geometry and/or pattern of the fixation point array is determined by the fixed physical configuration of the plurality of light sources 202.

Figure 3:
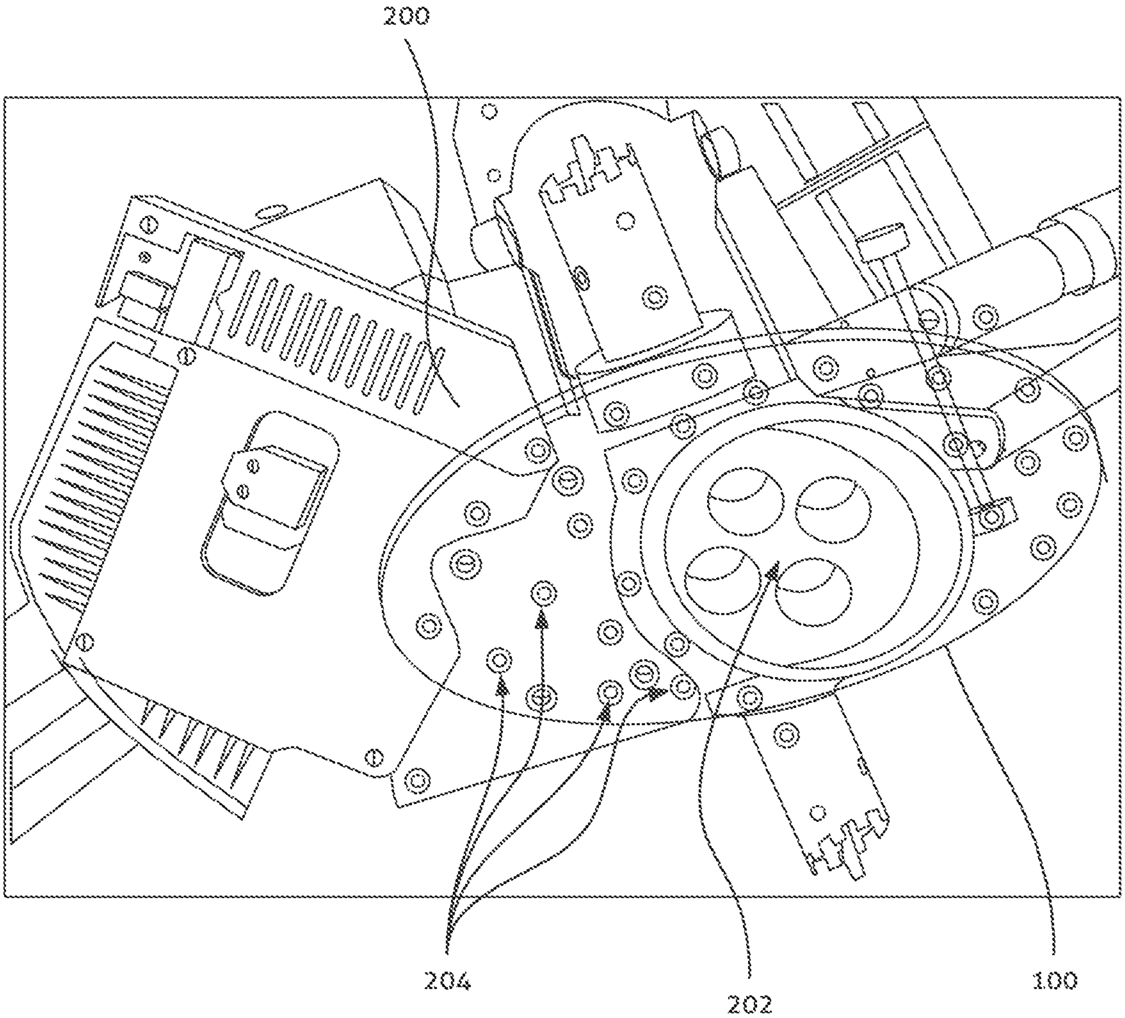
FIG. 3 illustrates an isometric view of a non-limiting example of an eye fixation assistance device consistent with certain embodiments of the present disclosure.

A variety of geometries may be used in connection with the eye fixation assistance device 100. FIG. 3 illustrates an isometric view of a non-limiting example of an eye fixation assistance device 100 consistent with certain embodiments of the present disclosure. As discussed in more detail below, the eye fixation assistance device 100 may comprise a base plate providing the structure to the eye fixation assistance device 100. The base plate may, in some embodiments, surround and/or otherwise encircle at least a portion of an optical objective and/or an associated lens 202 of the microscope 200 without obstructing a surgical professional's view through the microscope 200. In further embodiments, the base plate may define an aperture and/or opening through which a surgical professional may view a patent's eye through via the objective and/or an associated lens 202 of the microscope 200 without obstruction.

In some embodiments, the opening and/or aperture defined by the base plate and/or the associated eye fixation assistance device 100 may be circular, although other suitable configurations may also be used, including those with non-circular openings and/or apertures. In some embodiments, the aperture and/or opening may be symmetrical around one or multiple axis and/or may have a geometry configured for a particular microscope 200 and/or objective and/or lens 202.

The specific geometry of the base plate of the eye fixation assistance device 100 and/or portions thereof may be configured in a number of suitable ways, which may depend on the geometry and/or configuration of a particular microscope 200 and/or objective and/or lens 202. For example, the position of the opening and/or aperture defined by the base plate and/or the associated eye fixation assistance device 100 may be centered around the base plate and/or associated eye fixation assistance device 100 and/or portions thereof, may be offset within the base plate and/or associated eye fixation assistance device 100 and/or portions thereof, may be located about one or more axis of symmetry of the base plate and/or associated eye fixation assistance device 100, and/or in any other desired configuration.

Figure 4:
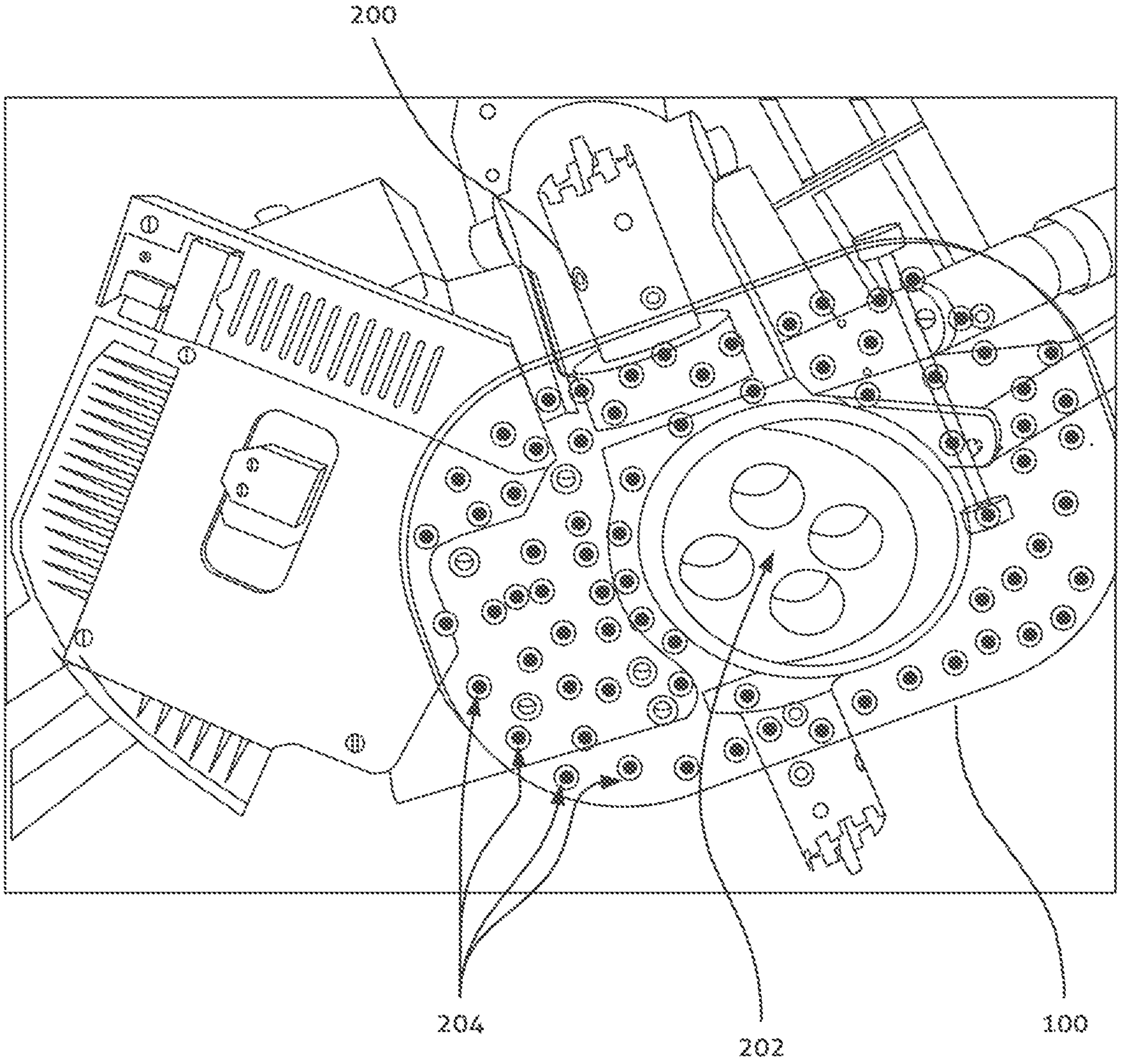
FIG. 4 illustrates an isometric view of a further non-limiting example of an eye fixation assistance device consistent with certain embodiments of the present disclosure.

For example and without limitation, FIG. 4 illustrates an isometric view of an eye fixation assistance device 100 consistent with certain embodiments of the present disclosure. As shown in FIG. 4, in some embodiments, the eye fixation assistance device 100 may be relatively symmetrical about two of its axis and may define an opening and/or aperture that is centered on the eye fixation assistance device 100. In further embodiments, as shown in FIG. 3, the opening and/or aperture defined by the eye fixation assistance device 100 may be offset in both axis, sized and configured to allow for a desired fixation point array geometry providing a variety of fixation points at different angles relative to the patient's eyes without obstructing the workspace for the surgeon. Thus, it will be appreciated that the geometry of the base plate and/or the associated eye fixation assistance device 100, the opening and/or aperture defined by the same, and/or the geometry and/or configuration of any associated fixation point arrays may vary in different implementations, with specific geometries and/or configurations being dependent on desired fixation point locations, surgical professional working space requirements, specific microscope geometries and/or configurations, and/or the like, without departing from the scope of the disclosed embodiments.

Figure 5:
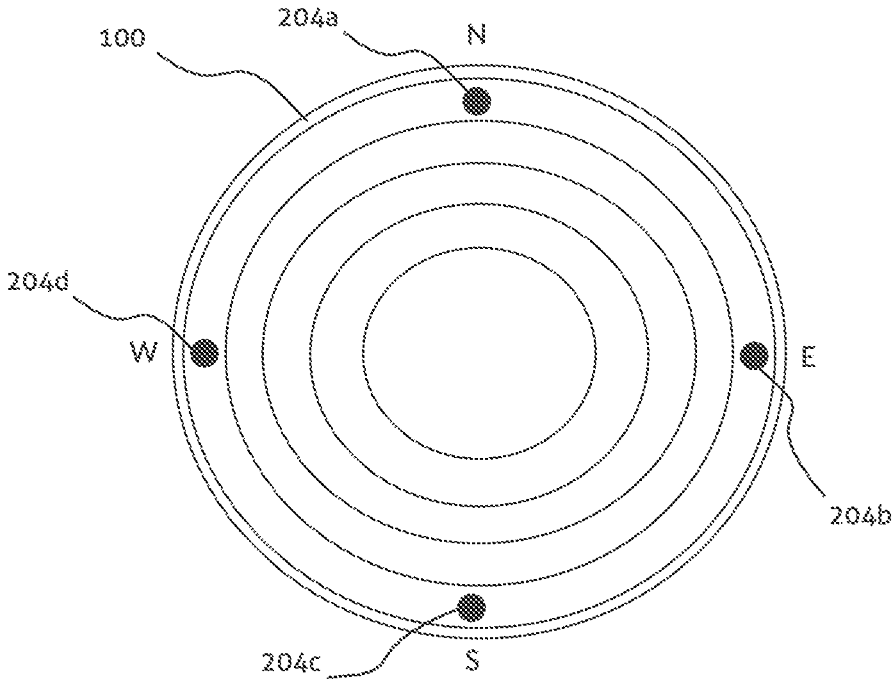
FIG. 5 illustrates a non-limiting example of fixation point configuration of an eye fixation assistance device consistent with certain embodiments of the present disclosure.

The fixation point array and/or plurality of light sources 204 may be arranged in a variety of suitable patterns relative to the microscope lens 202. FIG. 5 illustrates a non-limiting example of fixation point configuration of an eye fixation assistance device 100 consistent with certain embodiments of the present disclosure. As illustrated in this simplified example, the fixation point array may define four fixation points, marked for purposes of explanation with associated cardinal directions. Each fixation point may be associated with a selectively illuminable light source **204*a*-204*d*. By selectively illuminating one of the light sources 204*a*-204*d*, a surgical professional may direct a patient to fix and/or otherwise orient their eyes in the direction of the desired fixation point. For example, if a surgical professional desires that a patient orient their eye towards the marked cardinal direction North, light source 204*a* may be illuminated. Similarly, if a surgical professional desires that a patient orient their eye towards the marked cardinal direction South, light source 204*c*** may be illuminated.

Figure 6:
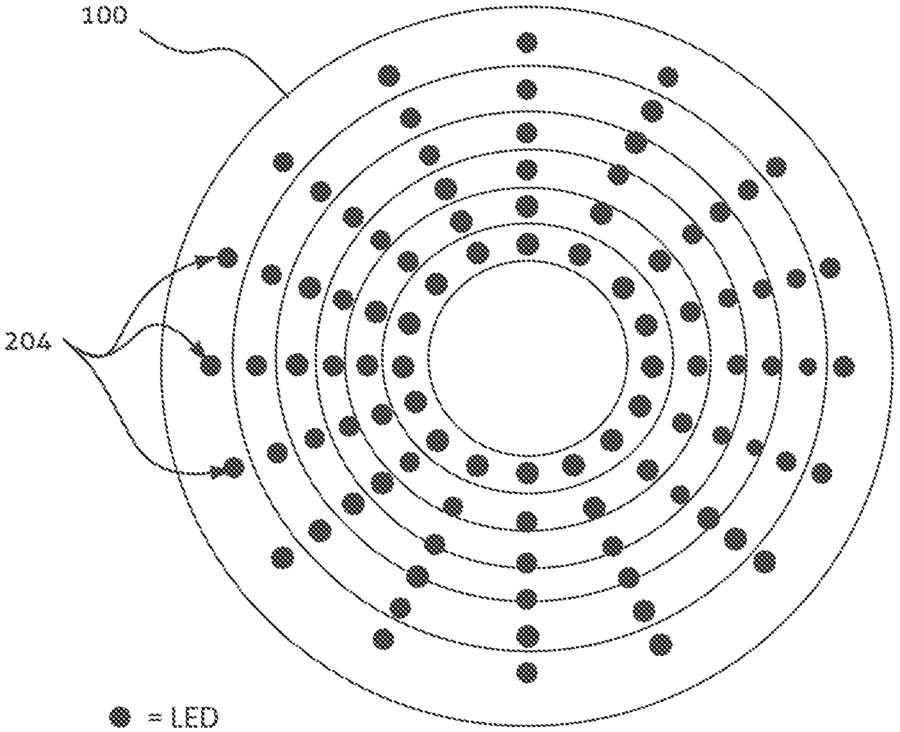
FIG. 6 illustrates a further non-limiting example of fixation point configuration of an eye fixation assistance device consistent with certain embodiments of the present disclosure.

More complex fixation point array geometries and/or configurations may also be used. FIG. 6 illustrates a further non-limiting example of fixation point configuration of an eye fixation assistance device 100 consistent with certain embodiments of the present disclosure. As illustrated, the fixation point array may define a plurality of fixation points arranged in a plurality of concentric circles surrounding and/or radial lines extending outwards from the microscope lens 202 and/or the associated opening and/or aperture, which each fixation point being associated with a selectively illuminable light source 204. In various embodiments, having a number of fixation points in various locations and/or configurations surrounding the microscope lens 202 may provide more fixation point options for a surgical professional to direct the patient to orient their eye/gaze towards.

In certain embodiments, in addition to use in guiding patient eye fixation, the illuminable light source(s) 204 may be used as a guide for a surgical professional. For example, a concentric ring reflection (or other suitable pattern) from the light source(s) on the patient's eye may be perceivable by the surgical professional allowing them to, for example and without limitation, create incisions and/or align toric lenses. In some implementations, different light source colors may be used to indicate different positions (e.g., degrees in a circle).

Figure 7:
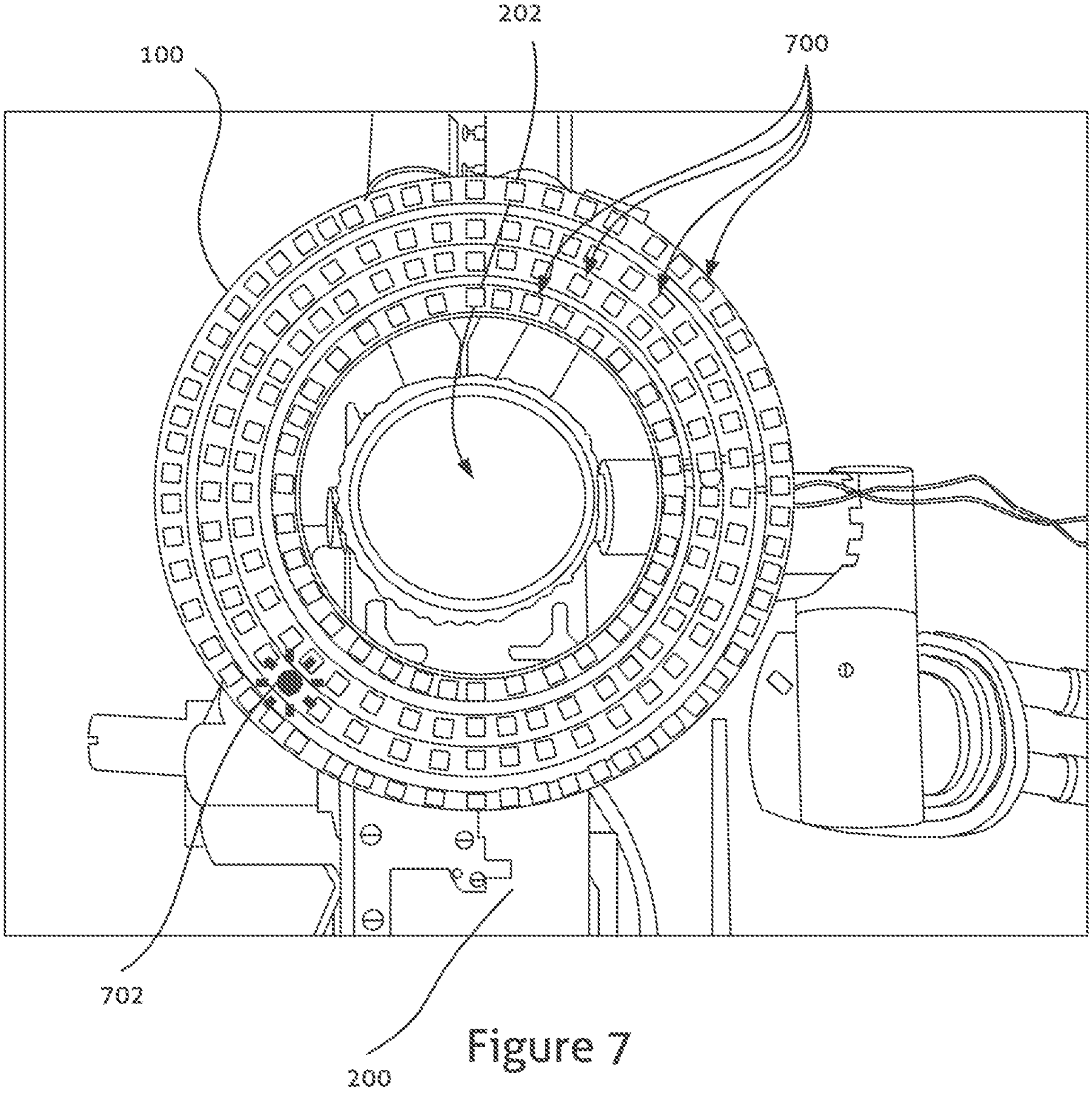
FIG. 7 illustrates a non-limiting example of an eye fixation assistance device attached to a microscope viewed from the perspective of a patient consistent with certain embodiments of the present disclosure.

FIG. 7 illustrates a non-limiting example of an eye fixation assistance device 100 attached to a microscope 200 viewed from the perspective of a patient consistent with certain embodiments of the present disclosure. In some embodiments, the fixation point array defined by the eye fixation assistance device 100 may define fixation points at locations surrounding the microscope lens 202, allowing the surgical professional with a 360 range of potential fixation points to direct a patient towards surrounding the microscope lens 202. For example, as illustrated, the fixation point array may comprise an LED array 700. The LED array 700 may comprise a plurality of strips of LEDs arranged in concentric circles surrounding the microscope lens 202 and/or the aperture defined by the eye fixation assistance device 100 and/or an associated base plate.

Consistent with embodiments herein, a surgical professional may selectively illuminate one or more of the LEDs of the LED array 700 using a suitable control system. For example, as illustrated, a surgical professional may selectively illuminate LED 702. A patient may visually perceive that LED 702 is illuminated and orient and/or otherwise direct their eye towards the illuminated fixation point. In this manner, the patient may fix and/or otherwise orient their eye in a direction desired by the surgical professional during an ophthalmic procedure. In various embodiments, the location, color, intensity, and/or illumination pattern of the illuminated LED 702 (e.g., flashing pattern) may be controlled by the surgical professional as desired, providing further visual communications and/or queues to their patients.

Figure 8:
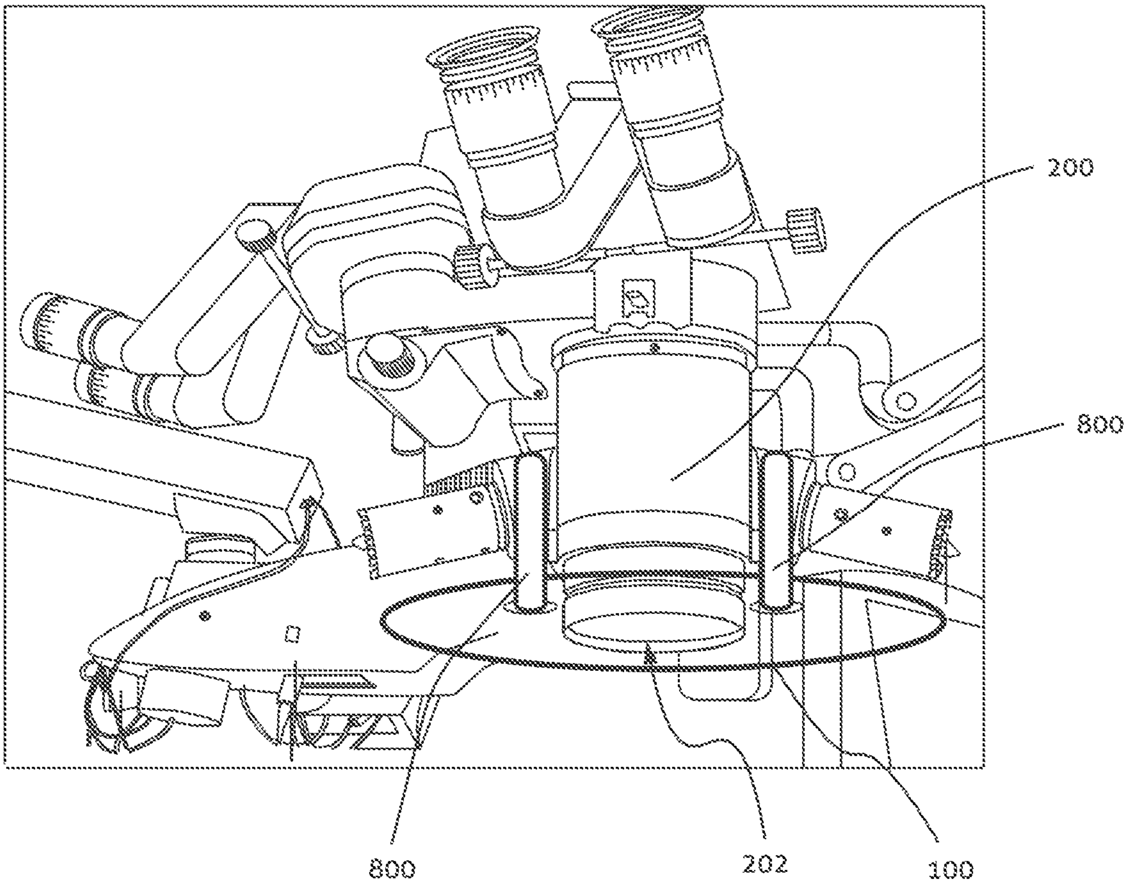
FIG. 8 illustrates a non-limiting example of an attachment mechanism for an eye fixation assistance device consistent with certain embodiments of the present disclosure.

The eye fixation assistance device 100 (and/or a base plate of the same) may be attached and/or otherwise coupled to a microscope 200 via a suitable attachment mechanism. FIG. 8 illustrates a non-limiting example of an attachment mechanism 800 for an eye fixation assistance device 100 consistent with certain embodiments of the present disclosure. As illustrated, the eye fixation assistance device 100 and/or an associated baseplate may be attached and/or otherwise coupled to the microscope 200 via one or more hooks and/or straps 800. In the illustrated example, the hooks and/or straps 800 may attach to handlebars of the microscope 200, securing the eye fixation assistance device 100 and positioning the eye fixation assistance device 100 relative to the microscope 200.

Figure 9:
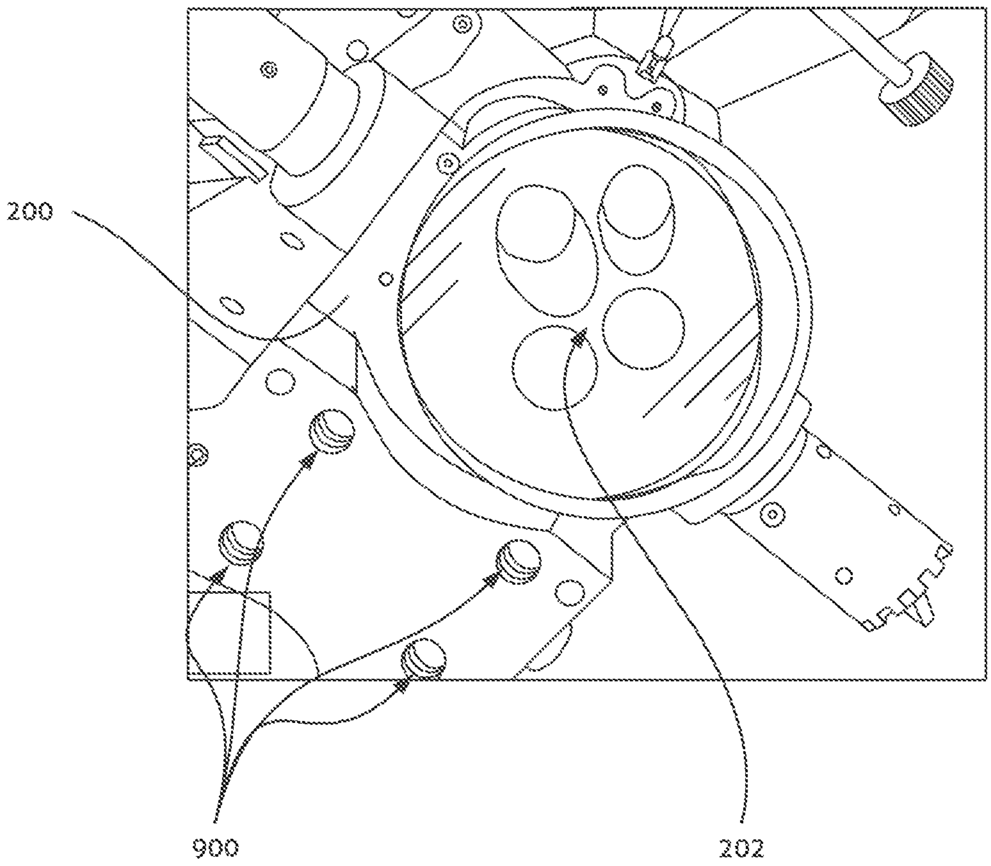
FIG. 9 illustrates a non-limiting example of attachment points on a microscope for an eye fixation assistance device consistent with certain embodiments of the present disclosure.

In further embodiments, one or more defined attachment points on a microscope 200 may be used. FIG. 9 illustrates a non-limiting example of attachment points 900 on a microscope 200 for an eye fixation assistance device consistent with certain embodiments of the present disclosure. As shown, the microscope 200 may be configured with one or more integrated attachment points 900 for coupling various accessory devices to the microscope 900. In some embodiments, the attachment points 900 may comprise threaded connection points allowing for devices and/or accessories (e.g., the eye fixation assistance device disclosed herein) to be bolted and/or otherwise affixed to the microscope at the attachment points 900, although other suitable types of connection points may also be used.

Figure 10:
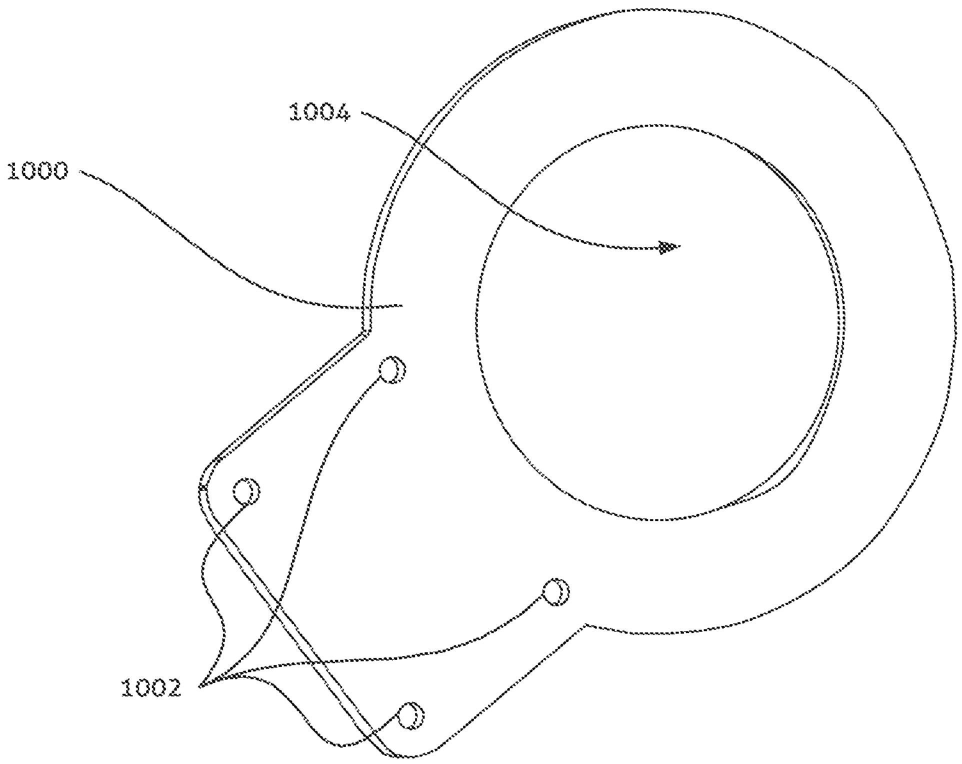
FIG. 10 illustrates a non-limiting example of a base plate of an eye fixation assistance device consistent with certain embodiments of the present disclosure.

The eye fixation assistance device and/or an associated baseplate may have complementary geometry allowing for attachment and/or coupling of the device/baseplate to the microscope 200 via the attachment points 900. FIG. 10 illustrates a non-limiting example of a base plate 1000 of an eye fixation assistance device consistent with certain embodiments of the present disclosure. As illustrated, the base plate 1000 may define one or more attachment points 1002, which may be used to couple the base plate 1000 to the microscope at complementary attachment points. For example, in some embodiments, the attachment points 1002 may comprise one or more holes (which in certain implementations may be threaded) allowing one or more bolts to pass through allowing for the base plate 1000 to be secured to the microscope at complementary threaded attachment points (or in some configurations if nuts and/or washers are used, via non-threaded attachment points). In this manner, the attachment points 1002 may be used to attach, position, and/or otherwise secure the base plate 1000 to the microscope in an installed position.

It will be appreciated that a variety of mechanisms may be used to couple to eye fixation assistance device and/or associated base plate 1000 to a microscope, which may depend on the relative geometries and/or configurations of the eye fixation assistance device, associated base plate 1000, and/or the microscope. In further embodiments, the eye fixation assistance device 100 may not attach and/or otherwise be coupled to the microscope 200 directly, but instead may be attached to some other suitable piece of equipment and/or positioning structure(s) (e.g., an independent stand and/or the like).

As detailed above, the base plate 1000 may provide structure to the disclosed eye fixation assistance device, allowing for mounting of the eye fixation assistance device to a microscope and/or other suitable equipment and/or structures and defining an opening and/or aperture 1004 allowing for the surgical professional to view a patient's eye without obstruction. The base plate 1000 may further provide structure for mounting and/or otherwise coupling the fixation point array and/or associated light sources to the base plate 1000.

The base plate 1000 may be formed using a variety of suitable materials including, for example and without limitation, plastic, metal, and/or composite materials. In some embodiments, the base plate 1000 and/or other associated components of the eye fixation assistance device may be sterilizable without impacting the integrity and/or finish of the base plate 1000 and/or other components. The base plate 1000 and/or other components may be formed in a variety of suitable ways including, for example and without limitation, using casting, machining, and/or the like.

Figure 11:
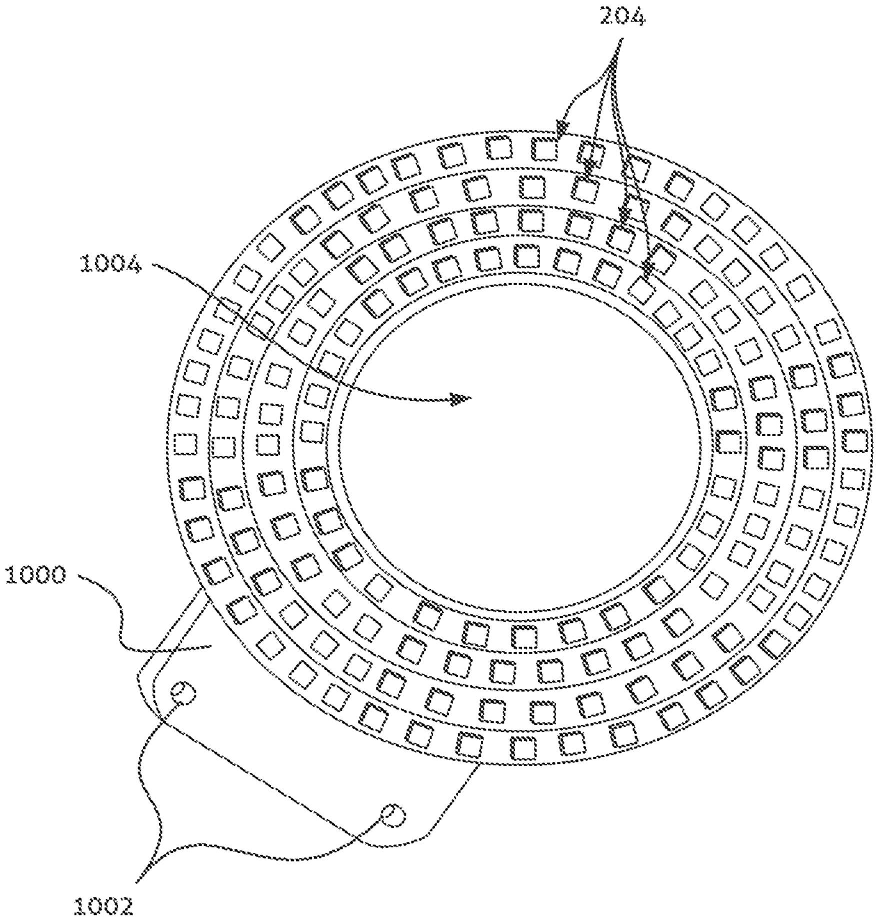
FIG. 11 illustrates a non-limiting example of a fixation point array and associated light sources attached to an eye fixation assistance device base plate consistent with certain embodiments of the present disclosure.

FIG. 11 illustrates a non-limiting example of a fixation point array and associated light sources 204 attached to an eye fixation assistance device base plate 1000 consistent with certain embodiments of the present disclosure. The base plate 1000 may provide structure for mounting and/or otherwise coupling the fixation point array and/or associated light sources 204 to the base plate 1000. The fixation point array and/or associated light sources 204 may be mounted and/or otherwise coupled to the base plate 1000 in a variety of suitable ways including, without limitation, one or more of adhesive mounting, physical coupling (e.g., via screws and/or other securement mechanisms, etc.), and/or the like.

Figure 12:
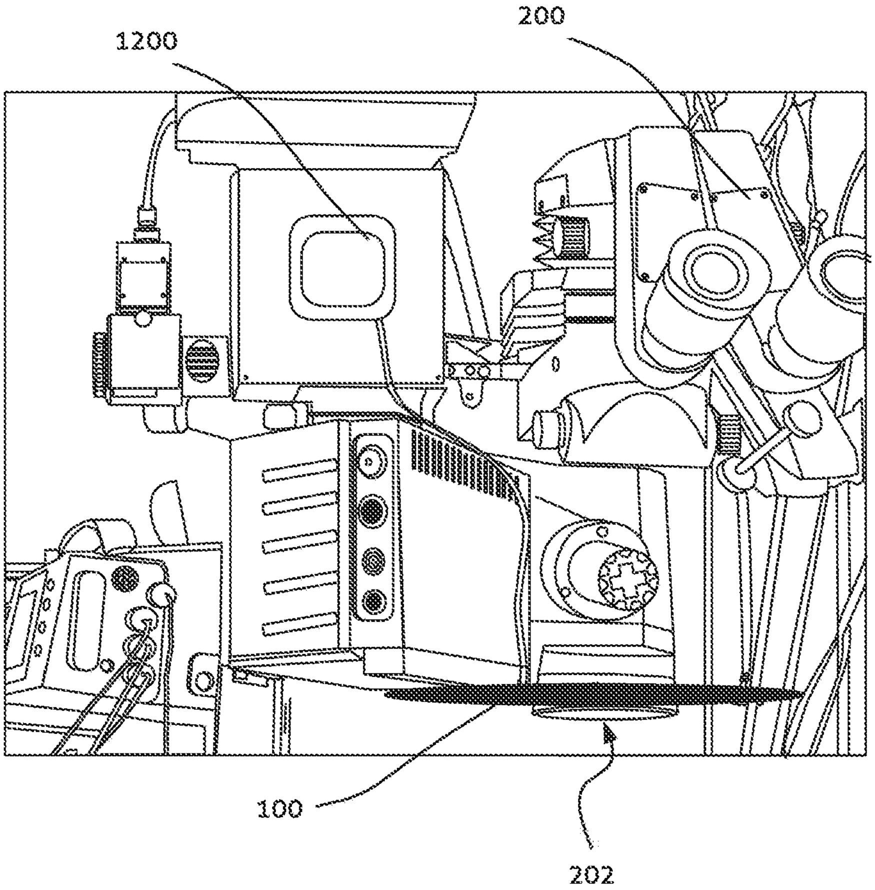
FIG. 12 illustrates a non-limiting example of control system configuration for an eye fixation assistance device consistent with certain embodiments of the present disclosure.

FIG. 12 illustrates a non-limiting example of control system 1200 configuration for an eye fixation assistance device 100 consistent with certain embodiments of the present disclosure. As illustrated, the control system 1200 may be communicatively coupled via a suitable communication channel (e.g., a wired and/or wireless communication channel) with the eye fixation assistance device 100. Consistent with embodiments herein, by interacting with the control system 1200, a surgical professional may selectively illuminate one or more light sources of a fixation point array included on the eye fixation assistance device 100.

The control system 1200 may be implemented in a variety of ways. For example, in some embodiments, the control system 1200 may comprise a discrete control device with suitable user interface(s) allowing the user to control the eye fixation assistance device 100 and/or components of the device 100 (e.g., one or more light sources). In further embodiments, the control system 1200 may comprise a mobile device (e.g., a smart phone, tablet, laptop computer) and/or other computing device (e.g., a desktop computer) running a suitable application to allow the user to control the eye fixation assistance device 100. In some embodiments, the control system 1200 may comprise a touch screen and/or other physical interface(s) (e.g., a mouse, joystick, foot pedal(s), foot tracking pad, etc.) allowing the user to control the eye fixation assistance device 100.

In further embodiments, the control system 1200 may comprise one or more voice command interfaces, which may allow a user to control the eye fixation assistance device 1000 via verbally issued commands and/or direction. For example and without limitation, voice commands such as "eye position, three o'clock" may be issued by a surgical professional to the control system 1200, which may recognize the voice commands (e.g., using artificial intelligence voice recognition engines) to activate corresponding light sources of the eye fixation assistance device 100.

In some embodiments, the control system 1200 may be mounted and/or otherwise coupled to the microscope 200. The control system 1200 may be mounted and/or otherwise coupled to the microscope 200 in a variety of suitable ways including, without limitation, one or more of adhesive mounting, physical coupling (e.g., via screws and/or other complementary securement mechanisms, etc.), and/or the like. In further embodiments, the control system 1200 may not be attached and/or otherwise be coupled to the microscope 200 directly, but instead may be attached to some other suitable piece of equipment and/or positioning structure(s) (e.g., an independent stand and/or the like).

Figure 13:
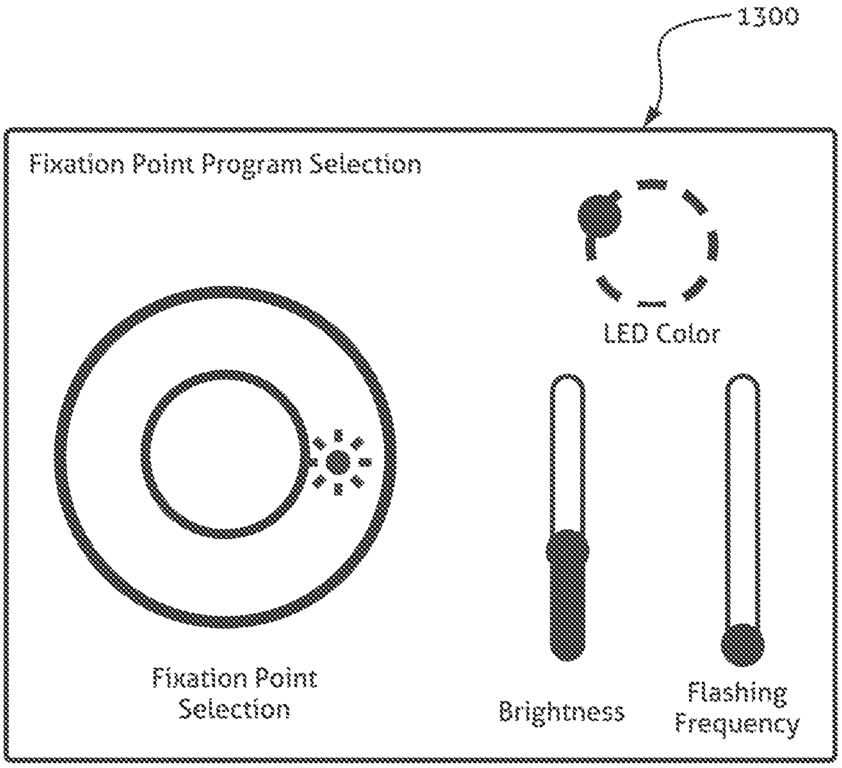
FIG. 13 illustrates a non-limiting example of control system interface for an eye fixation assistance device consistent with certain embodiments of the present disclosure.

FIG. 13 illustrates a non-limiting example of control system interface 1300 for an eye fixation assistance device consistent with certain embodiments of the present disclosure. In the illustrated embodiments, a touch screen may be used to control various function of the eye fixation assistance device. For example, a graphical representation of the eye fixation assistance device may be provided that allows a user to select and/or control (e.g., via a touch operation) one or more locations where fixation point light sources are to be illuminated on the eye fixation assistance device.

In some embodiments, the interface 1300 may control each light source of the fixation point array individually. In further embodiments, the interface 1300 may control clusters of light sources (e.g., as may be the case if a cluster of light sources form a single fixation point). Although various embodiments and examples herein show a single fixation point and/or associated light source being activated, it will be appreciated that in further embodiments, multiple light sources of the fixation point array may be activated simultaneously if desired by the surgical professional.

Further controls of the interface 1300 may allow for varying light intensity and/or brightness, color, and/or flashing patterns (and/or associated flashing pattern frequency). For example and without limitation, the interface 1300 may be capable of activating the light sources in a pattern, such as a fixed pattern (e.g., activated indefinitely), flashing pattern (e.g., activated and deactivated at regular time intervals), group flashing pattern (e.g., groups of light sources activated and deactivated at regular time intervals). For example, in some implementations, a fixed and/or flashing ring formation may be used to direct a patient to stabilize their eye fixation on the center of the microscope.

In yet further embodiments, certain sequential programs of varied fixation point patterns and/or series of patterns may be selected via the control interface 1300. In some embodiments, such programs may be associated with a particular procedure (and indeed, in some cases, may be pre-programmed). In further embodiments, programs may be dynamically defined and/or otherwise created by a surgical professional based on procedural preferences.

Figure 14:
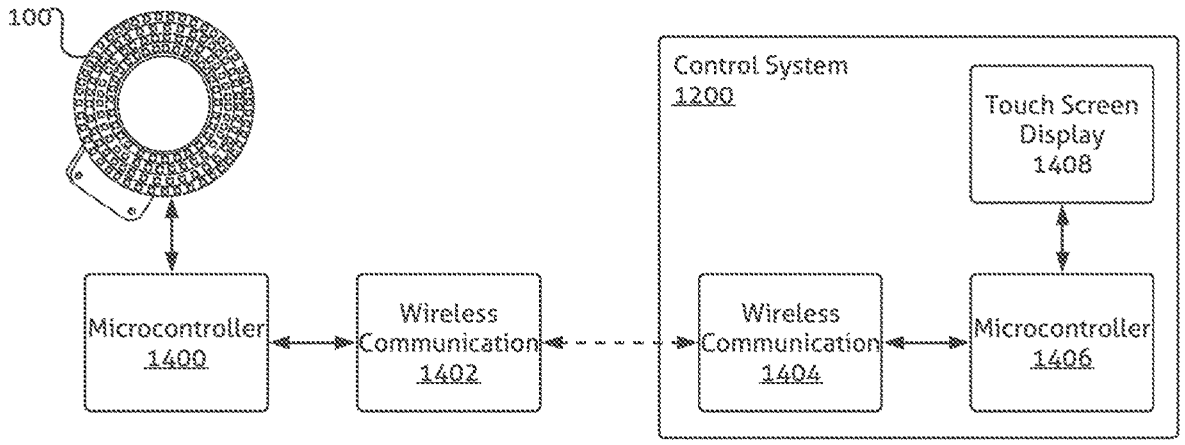
FIG. 14 illustrates a first non-limiting example of communication between a control system and an eye fixation assistance device consistent with certain embodiment disclosed herein.

The control system may be communicatively coupled with the eye fixation assistance device in a variety of ways. FIG. 14 illustrates a first non-limiting example of communication between a control system and an eye fixation assistance device consistent with certain embodiment disclosed herein. In the illustrated example, the control system 1200 may communicate with the eye fixation assistance device 100 via a wireless communication channel.

The control system 1200 may comprise a microcontroller 1406 and/or other processor configured to execute various control system functionality, including facilitating user interaction via a touch screen display 1408 and/or communication with the eye fixation assistance device 100 via a control system wireless communication module 1404. The eye fixation assistance device 100 may comprise a microcontroller 1400 configured to execute various functionality of the eye fixation assistance device 100 (e.g., controlling light sources of the fixation point array) based on control signals received from the control system 1200 via a wireless communication module 1402. Although illustrated as separate components from the eye fixation assistance device, it will be appreciated that the microcontroller 1400 and/or wireless communication module 1402 may be integrated in the eye fixation assistance device 100 and/or portions thereof.

A variety of suitable wireless standards may be used by the wireless communication modules 1402, 1404 including, for example and without limitation, IEEE's 802.11 standards, Bluetooth®, ultra-wide band ("UWB"), Zigbee®, 2.4 GHz operating band, 5 GHz operating band, and or any other suitable standard or combination of standards. In various embodiments, use of wireless communication channels between the control system 1200 and the eye fixation assistance device 100 may provide certain flexibility in mounting and/or otherwise locating the control system 1200 relative to the eye fixation assistance device 100. Although not specifically illustrated, it will be appreciated that the control system 1200 and/or the eye fixation assistance device 100 may be powered via a variety of ways, including using battery power (e.g., using rechargeable lithium batteries) and/or via corded power sources (e.g., USB powered).

Figure 15:
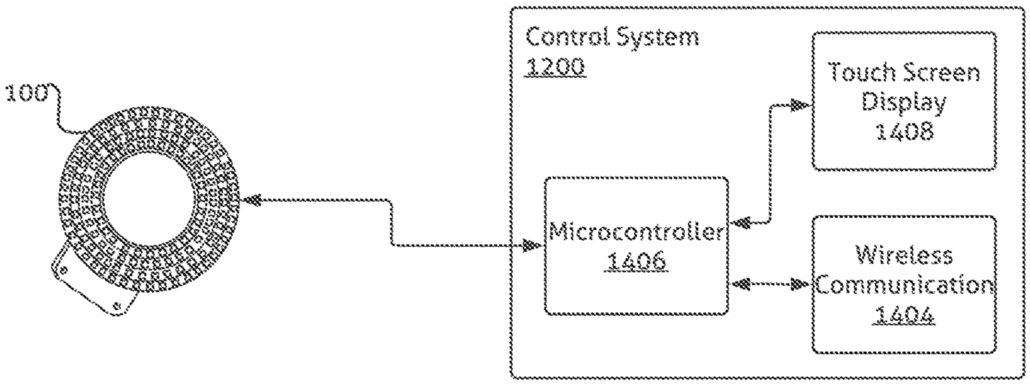
FIG. 15 illustrates a second non-limiting example of communication between a control system and an eye fixation assistance device consistent with certain embodiment disclosed herein.

FIG. 15 illustrates a second non-limiting example of communication between a control system 1200 and an eye fixation assistance device 100 consistent with certain embodiment disclosed herein. In the illustrated example, a wired communication channel may be used between the control system 1200 and the eye fixation assistance device 100, with a microcontroller 1406 included in the control system 1200 directly controlling the eye fixation assistance device 100 and/or associated light sources of a fixation point array based on input received via a touch screen display 1408. The control system 1200 may further include a wireless communication module 1404 which may be used to facilitate communication between the control system 1200 and/or other systems and/or services (e.g., for software updates, receiving fixation point sequential programs, etc.)

Figure 16:
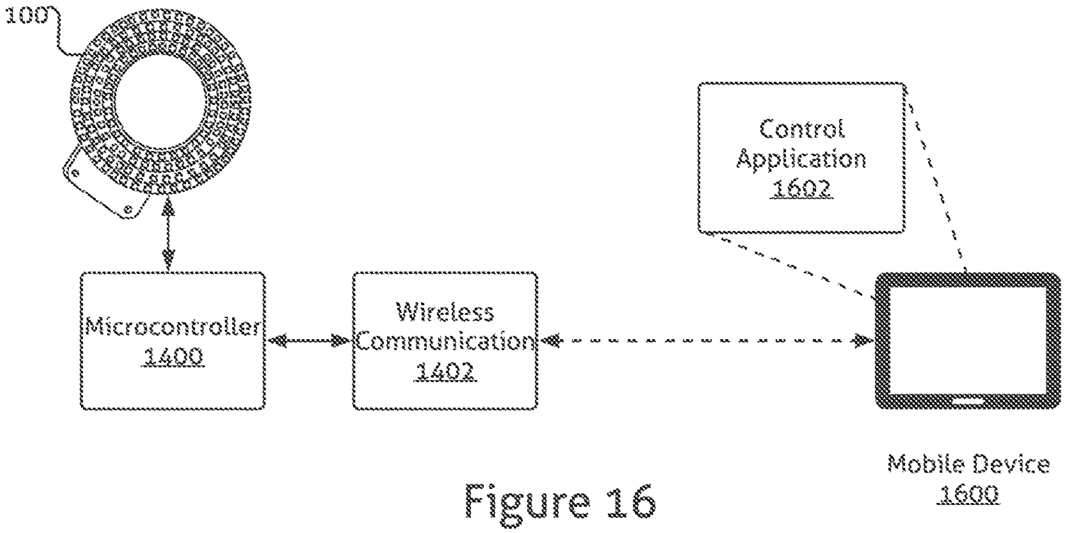
FIG. 16 illustrates a third non-limiting example of communication between a mobile device operating as control system and an eye fixation assistance device consistent with certain embodiment disclosed herein.

In certain embodiments, the control system 1200 may be implemented using a general-purpose computing device and/or system executing a control application. FIG. 16 illustrates a third non-limiting example of communication between a mobile device 1600 operating as control system and an eye fixation assistance device 100 consistent with certain embodiment disclosed herein. The mobile device 1600 may comprise, for example and without limitation, one or more of a smart phone, a tablet, a laptop computer, and/or the like, and/or any other computing device (e.g., desktop computer) running a control application 1602 to allow a user to control the control the eye fixation assistance device 100. The mobile device 1600 may issue commands wirelessly to a wireless communication module 1402 of the eye fixation assistance device 100 (and/or directly via a wired connection) that direct the microcontroller 1400 to execute various functionality of the eye fixation assistance device 100 (e.g., controlling light sources of the fixation point array).

Figure 17:
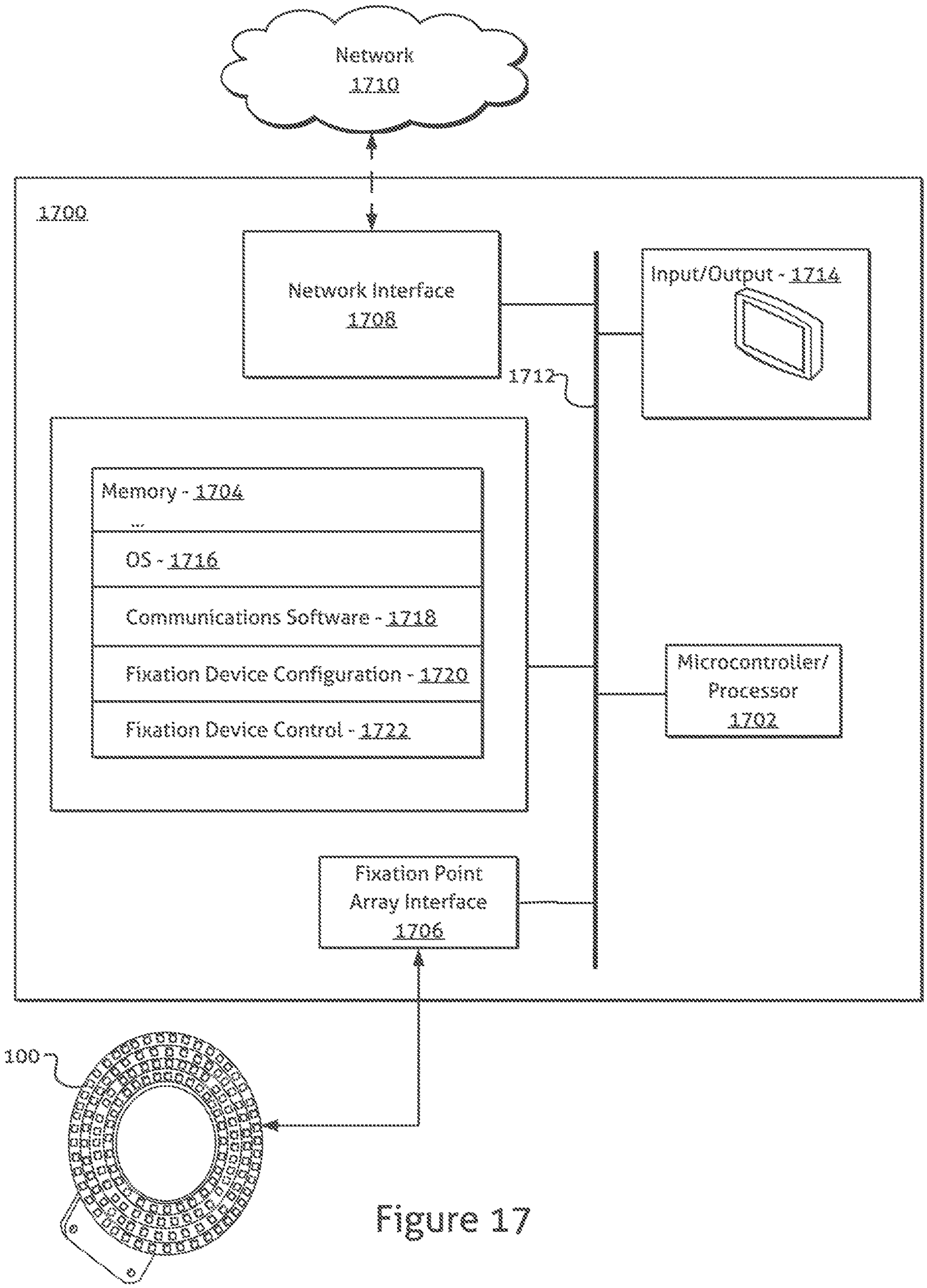
FIG. 17 illustrates a non-limiting example of a control system architecture that may be used to implement certain embodiments of the systems and methods of the present disclosure.

FIG. 17 illustrates a non-limiting example of a control system architecture that may be used to implement certain embodiments of the systems and methods of the present disclosure. The system 1700 of FIG. 17 and/or aspects thereof may be included in a system, service, and/or device associated with a control system, an eye fixation assistance device, and/or any other device, system, and/or service configured to implement embodiments of the disclosed systems and methods and/or aspects thereof.

The various systems and/or devices used in connection with aspects the disclosed embodiments may be communicatively coupled using a variety of networks and/or network connections (e.g., network 1710). In certain embodiments, the network 1710 may comprise a variety of network communication devices and/or channels and may utilize any suitable communications protocols and/or standards facilitating communication between the systems and/or devices. The network 1710 may comprise the Internet, a local area network, a virtual private network, and/or any other communication network utilizing one or more electronic communication technologies and/or standards (e.g., Ethernet or the like). In some embodiments, the network 1710 may comprise a wireless carrier system such as a personal communications system ("PCS"), and/or any other suitable communication system incorporating any suitable communication standards and/or protocols. In further embodiments, the network 1710 may comprise an analog mobile communications network and/or a digital mobile communications network utilizing, for example, code division multiple access ("CDMA"), Global System for Mobile Communications or Groupe Special Mobile ("GSM"), frequency division multiple access ("FDMA"), and/or time divisional multiple access ("TDMA") standards, 4G and/or 5G communication standards (e.g., Long-Term Evolution ("LTE"), 5G New Radio ("NR"), orthogonal frequency division multiple access ("OFDMA"), etc.). In certain embodiments, the network 1710 may incorporate one or more satellite communication links. In yet further embodiments, the network 1710 may utilize IEEE's 802.11 standards, Bluetooth®, ultra-wide band ("UWB"), Zigbee®, and or any other suitable standard or standards. The system 1700 may access the network 1700 using a suitable network interface 1708.

In certain embodiments, the systems and/or devices may comprise at least one processor system 1702, which may comprise a microcontroller, configured to execute instructions stored on an associated non-transitory computer-readable storage medium (e.g., system memory 1704). The systems and/or devices may further comprise software and/or hardware (e.g., network interface 1708) configured to enable electronic communication of information between the devices and/or systems via a network using any suitable communication technology and/or standard. Various components of the illustrated systems may be communicatively coupled via a bus 1712.

The operation of the system 1700 may be generally controlled by the processing unit 1702 operating by executing software instructions and programs stored in the system memory 1704 (and/or other computer-readable media, which may be removable). The system memory 1704 may store a variety of executable programs or modules for controlling the operation of the system. For example, the system memory may include an operating system ("OS") 1716 that may manage and coordinate, at least in part, various operations and/or system hardware resources and provide for common services for execution of various applications.

The system memory 1704 may further include, without limitation, communication software 1718 configured to enable in part communication with and by the system, eye fixation assistance device configuration modules 1720 configured to allow for configuration of an associated eye fixation assistance device 100 based on input received via a user interface 1714, eye fixation assistance device control modules 1722, and/or any other information, modules, and/or applications configured to implement embodiments of the systems and methods disclosed herein.

A fixation point array interface 1706 may couple (e.g., communicatively couple, power, etc.) the system 1700 to the eye fixation assistance device 100. Although illustrated as being separate from the network interface 1708, it will be appreciated that in some embodiments, the fixation point array interface 1706 and the network interface 1708 may be integrated in a single interface.

The systems and methods disclosed herein are not inherently related to any particular computer, control system, or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network.

Although the foregoing has been described in some detail for purposes of clarity, it will be apparent that certain changes and modifications may be made without departing from the principles thereof. For example, it will be appreciated that a number of variations can be made to the various embodiments, systems, services, and/or components presented in connection with the figures and/or associated description within the scope of the inventive body of work, and that the examples presented in the figures and described herein are provided for purposes of illustration and explanation, and not limitation. It is further noted that there are many alternative ways of implementing both the systems and methods described herein. Accordingly, the present embodiments are to be considered as illustrative and not restrictive, and the embodiments of the invention are not to be limited to the details given herein but may be modified within the scope and equivalents of the appended claims.

The invention claimed is:

1. An eye fixation assistance device for use with an ophthalmic surgery microscope, the eye fixation assistance device comprising:
- a base plate defining an opening configured to allow a lens of the ophthalmic surgery microscope to view a patient eye without obstruction, the base plate having a bottom surface;
- an attachment mechanism configured to physically secure the base plate to the ophthalmic surgery microscope, the attachment mechanism comprising one or more bolt base plate attachment points configured to interface with one or more threaded microscope attachment points of the ophthalmic surgery microscope; and
- a fixation point array coupled to the bottom surface of the base plate, the fixation point array being visible by the patient eye when the base plate is physically secured to the ophthalmic surgery microscope and comprising a plurality of light sources, each light source of the plurality of light sources being located at a possible fixation point and configured to be selectively illuminated based on one or more control signals received from a control system.

2. The eye fixation assistance device of claim 1, wherein each light source of the plurality of light sources comprises a light emitting diode.

3. The eye fixation assistance device of claim 2, wherein the light emitting diode comprises a multi-colored light emitting diode.

4. The eye fixation assistance device of claim 2, wherein each light source of the plurality of light sources comprises a plurality of light emitting diodes.

5. The eye fixation assistance device of claim 4, wherein the plurality of light emitting diodes comprise different colored light emitting diodes.

6. The eye fixation assistance device of claim 1, wherein the fixation point array comprises a display screen with each light source of the plurality of light sources being provided by the display screen.

7. The eye fixation assistance device of claim 1, wherein the attachment mechanism comprises one or more hooks configured to attach to one or more handlebars of the ophthalmic surgery microscope.

8. The eye fixation assistance device of claim 1, wherein the attachment mechanism is integrally formed in the base plate.

9. The eye fixation assistance device of claim 1, wherein the opening comprises an aperture configured to surround the lens of the ophthalmic surgery microscope.

10. The eye fixation assistance device of claim 9, wherein the plurality of light sources are arranged in a circle surrounding the aperture.

11. The eye fixation assistance device of claim 9, wherein the plurality of light sources are arranged in a plurality of concentric circles surrounding the aperture.

12. The eye fixation assistance device of claim 1, wherein the plurality of light sources are arranged in a Cartesian grid.

13. The eye fixation assistance device of claim 1, wherein a brightness of each light source of the plurality of light sources may be selectively adjusted based on the one or more control signals received from the control system.

14. The eye fixation assistance device of claim 1, wherein a color of each light source of the plurality of light sources may be selectively adjusted based on the one or more control signals received from the control system.

15. The eye fixation assistance device of claim 1, wherein a flashing pattern of each light source of the plurality of light sources may be selectively adjusted based on the one or more control signals received from the control system.

16. The eye fixation assistance device of claim 1, wherein the one or more control signals are received from the control system via a wired communication channel.

17. The eye fixation assistance device of claim 1, wherein the one or more control signals are received from the control system via a wireless communication channel.

18. The eye fixation assistance device of claim 1, wherein the control system comprises a mobile device executing a control application.

* * * * *